United States Patent [19]

Ishibe et al.

[11] Patent Number: 5,449,825
[45] Date of Patent: Sep. 12, 1995

[54] PREPARATION OF HALOPERFLUORO AND PERFLUORO ETHERS

[75] Inventors: Nobuyuki Ishibe, Osaka, Japan; Tien K. Tran; Charles W. Martin, both of Lake Jackson, Tex.

[73] Assignee: The Dow Chemical Company, Midland, Mich.

[21] Appl. No.: 182,997

[22] Filed: Jan. 18, 1994

Related U.S. Application Data

[63] Continuation of Ser. No. 904,775, Jun. 25, 1992, abandoned.

[51] Int. Cl.⁶ .............................................. C07C 51/58
[52] U.S. Cl. ................................... 562/851; 568/615
[58] Field of Search ...................... 562/851; 568/615

[56] References Cited

U.S. PATENT DOCUMENTS

| | | |
|---|---|---|
| 3,132,123 | 5/1964 | Harris, Jr. et al. ............... 562/851 |
| 3,180,895 | 4/1965 | Harris, Jr. et al. ............... 562/851 |
| 3,282,875 | 11/1966 | Connolly et al. ................ 562/851 |
| 3,291,843 | 12/1966 | Fritz et al. ....................... 562/851 |
| 3,635,926 | 1/1972 | Gresham et al. ................ 562/851 |
| 3,943,112 | 3/1976 | Middleton ....................... 562/851 |
| 4,335,255 | 6/1982 | Krespan .......................... 562/851 |
| 4,499,249 | 2/1985 | Nakagawa et al. .............. 562/851 |
| 4,526,948 | 7/1985 | Resnick ........................... 562/851 |

FOREIGN PATENT DOCUMENTS

| | | |
|---|---|---|
| 0303292 | 2/1989 | European Pat. Off. . |
| 3715210 | 12/1987 | Germany . |
| 163507 | of 1979 | Japan . |
| 38231 | of 1983 | Japan . |

OTHER PUBLICATIONS

CA 113:131538 1990.

*Primary Examiner*—Paul J. Killos

[57] ABSTRACT

Process for preparing haloperfluoro and perfluoro ethers wherein a metal halide is reacted with a 3-haloperfluoropropene oxide to obtain a 2,3-dihaloperfluorocarbonyl fluoride; a metal halide, 2,3-dihaloperfluorocarbonyl fluoride and 3-haloperfluoropropene oxide are reacted to obtain a 2-(2',3'-dihaloperfluoropropoxy)-3-haloperfluoropropionyl fluoride; 2-(2',3'-dihaloperfluoropropoxy)-3-haloperfluoropropionyl fluoride is decarboxylated and dehalogenated to obtain perfluorovinylallylether. Alternatively, 2-(2',3'-dihaloperfluoropropoxy)-3-haloperfluoropropionyl fluoride is reacted with metal halide and 3-haloperfluoropropene oxide to obtain a 2-[2'-(2",3"-dihaloperfluoropropoxy)-3'-haloperfluoropropoxy]-3-haloperfluoropropionyl fluoride, or a higher polyether, and 2-[2'-(2",3"-dihaloperfluoropropoxy)-3'-haloperfluoropropoxy]-3-haloperfluoropropionyl fluoride or the polyether is decarboxylated and dehalogenated to obtain a 3,6-dioxa-5-halodifluoromethylperfluorenona-1,8-diene or the corresponding polyether.

32 Claims, No Drawings

PREPARATION OF HALOPERFLUORO AND PERFLUORO ETHERS

CROSS REFERENCE TO RELATED APPLICATION

This application is a continuation of Ser. No. 7/904,775, filed Jun. 25, 1992, now abandoned, which is incorporated in its entirety herein.

FIELD OF THE INVENTION

This invention relates to processes for the preparation of haloperfluoro and perfluoro ethers.

BACKGROUND OF THE INVENTION

Processes for preparing a variety of haloperfluoro and perfluoro ethers from a 3-haloperfluoropropene oxide have been discovered.

SUMMARY OF THE INVENTION

In one aspect, this invention involves a process for preparing an ether described by the formula

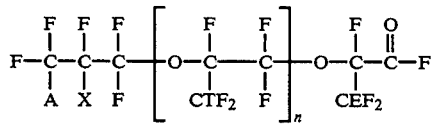

where A, T and E are each independently a fluorine, chlorine, bromine or iodine atom, X is a chlorine, bromine or iodine atom, and n is 0 to 6, comprising (a) preparing a 2,3-dihaloperfluoropropionyl fluoride by contacting an alkali metal chloride, bromide or iodide with a 3-haloperfluoropropene oxide in an inert liquid reaction medium, (b) coupling said 2,3-dihaloperfluoropropionyl fluoride to a 3-haloperfluoropropene oxide, (c) coupling the product of step (b) to n equivalents of a 3-haloperfluoropropene oxide, and (d) recovering the above described ether.

In a further aspect, this invention involves a process for preparing a vinyl ether described by the formula

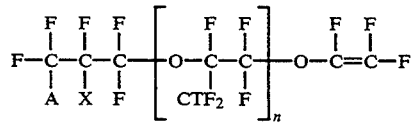

where A, T, X and n are as set forth above, comprising (a) preparing a 2,3-dihaloperfluoropropionyl fluoride by contacting an alkali metal chloride, bromide or iodide with a 3-haloperfluoropropene oxide in an inert liquid reaction medium, (b) coupling said 2,3-dihaloperfluoropropionyl fluoride to a 3-haloperfluoropropene oxide, (c) coupling the product of step (b) to n equivalents of a 3-haloperfluoropropene oxide, (d) decarboxylating the product of step (c), and (e) recovering said vinyl ether.

In a further aspect, this invention involves a process for preparing an allyl vinyl ether described by the formula

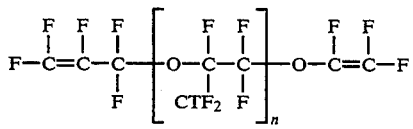

where T and n are as set forth above, comprising (a) preparing a 2,3-dihaloperfluoropropionyl fluoride by contacting an alkali metal chloride, bromide or iodide with a 3-haloperfluoropropene oxide in an inert liquid reaction medium, (b) coupling said 2,3-dihaloperfluoropropionyl fluoride to a 3-haloperfluoropropene oxide, (c) coupling the product of step (b) to n equivalents of a 3-haloperfluoropropene oxide, (d) decarboxylating the product of step (c), (e) dehalogenating the product of step (d), and (f) recovering said allyl vinyl ether.

In a further aspect, this invention involves the respective products of the above described processes.

The haloperfluoro and perfluoro ethers, diethers and polyethers containing vinyl unsaturation, or allyl and vinyl unsaturation, which are produced by the processes of this invention, are useful for polymerization with other ethylenically unsaturated monomers, such as tetrafluoroethylene, to prepare polymers. These polymers can be molded, formed or fabricated into articles or other finished goods of virtually any variety, particularly those for use in the automotive and electronics industries, or films or membranes. Polymers prepared from di- or polyethers, as described above, which have both allyl and vinyl unsaturation are especially useful because they can be cured (crosslinked) through the double bond which does not participate in polymerization and remains unreacted in a side chain. Articles which are fabricated from polymers prepared from such allyl vinyl ethers may be cured to impart the well known benefits of crosslinking. Other haloperfluoro ethers which are prepared by the processes of this invention are useful as intermediates in the preparation of the unsaturated haloperfluoro and perfluoro ethers and di- and polyethers of this invention.

DETAILED DESCRIPTION OF THE INVENTION

The various haloperfluoro ethers, diethers and polyethers which are prepared by the processes of this invention may be represented generally by the following formulae:

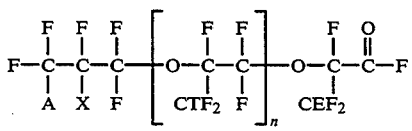

I

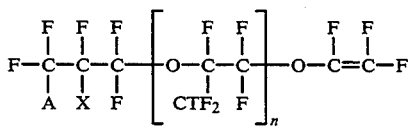

II

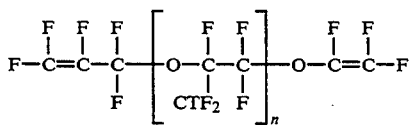

III where A, T, E, X and n are as set forth above. "Perfluoro" as used herein means that all the hydrogen atoms on a molecule (or independently named portion thereof), except those whose replacement would affect the nature of the characteristic groups present, have been replaced by fluorine atoms, except as otherwise noted by specific naming terminology.

Formula I represents an ether which can be decarboxylated to give the ether of Formula II. The ether of Formula II can be dehalogenated to give the ether of Formula III.

A 3-haloperfluoropropene oxide, which can be represented by a formula such as

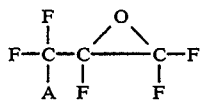

where A is as set forth above, is used as the starting material for preparation of the ethers of Formulae I to III. A 3-haloperfluoropropene oxide can be prepared by heating the corresponding 3-haloperfluoropropene with oxygen at superatmospheric pressure in the presence of an inert diluent, as is discussed further in Carlson, U.S. Pat. No. 3,536,733, which is incorporated herein in its entirety.

An ether of Formula I may be prepared from a 3-haloperfluoropropene oxide by first reacting same with a halide ion in a preliminary portion of Phase One of the processes of this invention to produce a 2,3-dihaloperfluoropropionyl fluoride. The 3-haloperfluoropropene oxide may be perfluoropropene oxide, 3-chloroperfluoropropene oxide, 3-bromoperfluoropropene oxide, or 3-iodoperfluoropropene oxide, however a preferred propene oxide for use as a starting material is 3-chloroperfluoropropene oxide. The 2,3-dihaloperfluoropropionyl fluoride obtained from the addition reaction between the halide ion and the propene oxide may be represented as follows:

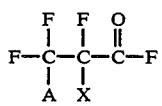

where A and X are as set forth above. A halide ion, X, from an alkali metal halide, MX (where M is an alkali metal ion), opens the 1,2 oxirane ring at the 2-carbon and adds at that position, displacing a fluorine atom from the 1-carbon.

The alkali metal ion, My may be lithium, sodium, potassium or cesium. In general, conversion of the 3-haloperfluoropropene oxide to the corresponding 2,3-dihaloperfluoropropionyl fluoride decreases with the increasing size of the metal ion, although in a sulfone-based liquid reaction medium, use of sodium may give as high if not higher a percent selectivity of addition to the 2-carbon than lithium.

The alkali metal halide (MX) is admixed with an inert liquid reaction medium, being one which is nonreactive with not only the starting materials (the alkali metal halide and the propene oxide in the preliminary portion of Phase One) but with the product (the propionyl fluoride) as well. Representative reaction media which are useful in these circumstances include glycol ethers such as $R^1$—O—[—$R^3$—O—]$_a$—$R^2$, where $R^1$ and $R^2$ are each independently a $C_1$–$C_6$ hydrocarbon radical such as methyl, ethyl, isopropyl, sec-butyl, neopentyl or cyclohexyl, $R^3$ is a $C_2$–$C_6$ hydrocarbon radical such as ethyl, isopropyl, sec-butyl, neopentyl or cyclohexyl, and a is 1 to 4; and sulfones such as sulfolane (tetrahydrothiopene-1,1-dioxide), 3methyl sulfolane, 3-sulfolene (2,5-dihydrothiopene-1,1dioxide), and dimethyl sulfone (sulfonylbismethane). Of these, the glycol ethers and sulfones are preferred, and tetraethylene glycol dimethyl ether and sulfolane are most preferred.

The liquid reaction medium is typically dried before use, for example over a molecular sieve. The alkali metal halide (MX) may be dissolved in the liquid reaction medium, or the two may be combined to form a slurry. The mixture is first heated to aid in the dispersion of the metal halide in the liquid reaction medium. The mixture is then cooled to a temperature of about −10° C. to about 40° C. With agitation, a 3-haloperfluoropropene oxide is added to the reaction mixture. For this purpose it may be bubbled or dripped into the reaction vessel as appropriate according to the temperature at which the reaction is being run. Addition of the 3-haloperfluoropropene oxide at a rate of about 0.1 mole per hour to about 10 moles per hour is continued, while maintaining a temperature of about 0° C. to about 30° C. until the desired amount has been added to the reaction mixture. The reaction may be run at atmospheric pressure, or may be run in a closed system or under vacuum, at a pressure of about 0.1 MPa to about 1 MPa.

The ratio of moles of metal halide per mole of 3-haloperfluoropropene oxide employed in the reaction may vary from about 1.0 to about 1.3. Use of metal halide in amounts substantially greater than this results in an increase in the relative percent yield of addition of the halide ion, X, to the 1-carbon atom, which is a by-product and not the desired result of the preliminary portion of Phase One. For example, when the mole ratio is about 3.0, it is not unknown for addition of the halide ion, X, to the 1-carbon atom to be the dominant form of the product by as much as 5 to 40 fold. When fluorine atoms have been displaced from both the 1and 2-carbons by the nucleophilic halide ion, X, a fluorine atom may be regenerated at the 1-carbon by contacting the resulting 2,3-dihaloperfluoropropionyl halide with fluoride ion.

The liquid reaction medium may be used in an amount of about 5 moles to about 50 moles per mole of metal halide. Any level of yield of the 2,3-dihaloperfluoropropionyl fluoride product is acceptable, but it is preferred that a yield of at least about 10 percent, and more preferably a yield of at least about 20 percent, based on the amount of 3-haloperfluoropropene oxide fed to the reaction system, be obtained.

Completion of the reaction to form the 2,3-dihaloperfluoropropionyl fluoride is indicated when the reaction ceases to generate heat.

In several exemplary runs, preparation of a 2,3-dihaloperfluoropropionyl fluoride in this preliminary portion of Phase One is demonstrated as follows: Dry alkali metal chloride powder is added to an inert liquid reaction medium which is first dried over a 4 Angstrom molecular sieve. The mixture is stirred under nitrogen and is cooled to a temperature of about −5° C. to about 0° C. To this slurried mixture is bubbled 3-chloroperfluoropropene oxide (80 to 90 percent pure) at a temperature of about 10° C. to about 25° C. over a period of about 0.5 to about 5 hours. One gram of

[4,7,13,16,21,24-hexaoxa-1,10-diazabicyclo(8.8.8)]hexacosane ("Krptofix 222"), a phase transfer agent, is also added in Run A-10. The mixture is thereafter allowed to attain ambient temperature and is evacuated to distill the volatile products into a receiver cooled with a dry ice/acetone mixture. The distillate is analyzed by gas chromatography to obtain the relative percent yield of the 2,3-dichloroperfluoropropionyl fluoride product and the 2,3-dichloroperfluoropropionyl chloride byproduct.

Fractional distillation gives more than 99 percent pure 2,3-dichlorotrifluoropropionyl fluoride with boiling point 49°–50° C. and more than 98 percent pure 2,3-dichlorotrifluoropropionyl chloride with boiling point 90°–91° C. Infrared spectra of the acid fluoride product shows the carbonyl stretching at 1,885 cm$^{-1}$ whereas those of the acid chloride exhibit it at 1,795 cm$^{-1}$. Analysis by $^{19}$F nuclear magnetic resonance of the acid fluoride shows a clear multiple at −95 ppm (relative to trifluoroacetic acid) derived from FC=O, which is not observed in the acid chloride.

The amount of 3-chloroperfluoropropene oxide ("Oxide"), the type and amount of alkali chloride, the type and amount of liquid reaction medium ("L.R.M."), the relative percent yield of the acid fluoride product and chloride byproduct, the mass of the distillate in grams, and the isolated percent yield of the acid fluoride are shown below in Table A for Runs A-1 to A-10, which illustrate preparation of a 2,3-dihaloperfluoropropionyl fluoride by this preliminary portion of Phase One of the processes of this invention.

Preparation of a 2,3-dihaloperfluoropropionyl fluoride in this preliminary portion of Phase One is also demonstrated in Runs B-1 to B-5, in which a metal bromide is used, as follows: Dried metal bromide powder is dispersed in an inert liquid reaction medium (L.R.M.). The metal bromide/L.R.M. mixture is stirred at 75° C. for 30 minutes. The mixture is then cooled to 40° C., and 3-chloropentafluoropropene oxide is added gradually over a 50 minute period. The temperature is maintained in a 28°–40° C. range during the addition of the 3-chloropentafluoropropene oxide. After the addition of 3-chloropentafluoropropene oxide is complete, the product is isolated by heating the flask to 50° C. under 29.8 inches Hg vacuum with collection in a −78° C. cold trap.

The distilled product shows the carbonyl absorption at 1,869 cm$^{-1}$ due to the acid fluoride. $^{19}$F nuclear magnetic resonance spectrum of the distilled product exhibits a similar pattern to 2,3-dichlorotrifluoropionyl fluoride and a multiple at −99 ppm (relative to trifluoroacetic acid).

The amount of 3-chloroperfluoropropene oxide ("Oxide"), the type and amount of alkali bromide, the type and amount of liquid reaction medium ("L.R.M."), the relative percent yield of the acid fluoride and other materials as byproducts, the mass of the distillate in grams, and the isolated percent yield of the acid fluoride are shown below in Table B for Runs B-1 to B-4.

TABLE B

| Run | Oxide[1] g(mole) | MBr g(mole) | Solvent[2] (ml) | Relative Yield[3] Fluoride | Relative Yield[3] Other | Distillate[4] g | Yield[5] % |
| --- | --- | --- | --- | --- | --- | --- | --- |
| B-1 | 79 (0.55) | LiBr, 43(0.5) | Sulfolane (950) | 74 | 26 | 35 | 21.4 |
| B-2 | 79 (0.55) | NaBr, 154.5 (1.5) | Sulfolane (2,500) | 59 | 33 | 114 | 18.5 |
| B-3 | 79 (0.55) | NaBr, 51.5 (0.5) | TGME (1,000) | 77 | 5 | 50 | 31.8 |
| B-4 | 79 (0.55) | KBr, 59.5 (0.5) | Sulfolane (950) + Me Sulfolane (50) | 40.1 | 43 | 36 | 11.9 |

[1]Epoxide = 3-Chloropentafluoropropene oxide.
[2]Me Sulfolane = 3-Methylsulfolane. TGME = Tetraethylene glycol dimethyl ether
[3]CG % area. Fluoride = 2-bromo-3-chlorotrifluoropropionyl fluoride.
[4]Flash distillate from the reaction mixture.
[5]Based on the distillate quantity and the GC area %.

In the concluding portion of Phase One, an ether of Formula I where n=0 may be prepared from the 2,3-dihaloperfluoropropionyl fluoride produced in the preliminary portion, as described above, by charging alkali fluoride (MF) to the reaction vessel and resuming the feed of 3-haloperfluoropropene oxide. The fluoride ion produces a stable alkoxide ion at the carbonyl carbon of the 2,3-dihaloperfluoropropionyl fluoride. This alkox-

TABLE A

| Run | Oxide[1] g(mole) | Alkali Chloride g(mole) | Relative Yield of L.R.M. (ml) | Acid Halide (%)[2] Fluoride[3] | Acid Halide (%)[2] Chloride[4] | Distillate grams | Isolated % Yield of Acid Fluoride |
| --- | --- | --- | --- | --- | --- | --- | --- |
| A-1 | 183 (0.1) | LiCl, 5.5 (0.13) | Sulfolane (100) | 13.5 | 71.7 | 14.2 | 9.3 |
| A-2 | 183 (0.1) | NaCl, 17.5 (0.3) | Sulfolane (100) | 49.1 | 34.8 | 7.2 | 17.7 |
| A-3 | 366 (0.2) | KCl, 16.4 (0.22) | Sulfolane (600) | 9.4 | 67.0 | 8.0 | 1.9 |
| A-4 | 183 (0.1) | CsCl, 50.4 (0.3) | Sulfolane (400) | 1.1 | 44.5 | 1.0 | 0.06 |
| A-5 | 119 (0.65) | LiCl, 32 (0.75) | Sulfolane (1,100) | 15.0 | 82.8 | 75 | 4.0 |
| A-6 | 256 (1.4) | LiCl, 64 (1.5) | Tetraglyme[5] (2,300) | 75.0 | 14.2 | 175 | 47.6 |
| A-7 | 256 (1.4) | LiCl, 64 (1.5) | Tetraglyme[5] (2,200) | 78.9 | 19.9 | 206 | 58.9 |
| A-8 | 138 (0.76) | LiCl, 64 (1.5) | Tetraglyme[5] (2,500) | 14.5 | 84.1 | 46 | 4.4 |
| A-9 | 255 (1.4) | LiCl, 64 (1.5) | Tetraglyme[6] (2,500) | 38.1 | 6.5 | 103 | 29.8 |
| A-10 | 128 (0.7) | LiCl, 32 (0.75)[7] | Tetraglyme[5] (1,100) | 77.9 | 20.6 | 99 | 59.0 |

[1]3-Chloroperfluoropropylene oxide
[2]Relative area of chromatograms
[3]2,3-Dichloroperfluoropropionyl fluoride
[4]2,3-Dichloroperfluoropropionyl chloride
[5]Tetraethylene glycol dimethyl ether
[6]Tetraethylene glycol diethyl ether
[7]Krptofix 222 (1 g) added ide ion opens the oxirane ring at the 2-carbon of the 3-haloperfluoropropene oxide to generate a carbonyl group in a manner similar to that by which the 2,3-dihaloperfluoropropionyl fluoride is itself produced from 3-haloperfluoropropene oxide in the preliminary portion of Phase One. Occurrence of the desired addition of the alkoxide ion at the 2-carbon of the 3-haloperfluoropropene oxide couples the carbonyl fluoride and the propene oxide, and provides an ether functionality in the molecule in addition to regenerating a carbonyl fluoride. The concluding portion of Phase One of the process yields a 2-(2',3'-dihaloperfluoropropoxy)-3-haloperfluoropropionyl fluoride an ether of Formula I where n=0, which is generally represented by a formula such as

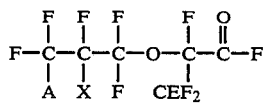

where A, E and X are as set forth above.

To prepare a 2-(2',3'-dihaloperfluoropropoxy)-3-haloperfluoropropionyl fluoride, addition of propene oxide to the reaction mixture is made at a rate of about 0.2 moles per hour to about 2 moles per hour. While maintaining a temperature of about −10° C. to about 25° C., 3-haloperfluoropropene oxide is added to the reaction mixture in an amount of about 0.9 moles to about 1.3 moles per mole of the 2,3-dihaloperfluoropropionyl fluoride, as produced, for example, in the preliminary portion of Phase One, as described above. The additional charge of alkali metal fluoride is made to the reaction mixture in an amount of about 0.01 moles to about 0.3 moles per mole of 2,3-dihaloperfluoropropionyl fluoride. The liquid reaction medium, as described above with relation to the preliminary portion of Phase One, may be present in the reaction mixture in an amount of about 2 moles to about 10 moles per mole of 2,3-dihaloperfluoropropionyl fluoride. The reaction may be run at atmospheric pressure, or may be run in a closed system or under vacuum, at a pressure of about 0.1 MPa to about 1 MPa. Any level of yield of the 2-(2',3'-dihaloperfluoropropoxy)- 3-haloperfluoropropionyl fluoride product is acceptable, but it is preferred that a yield of at least about 10 percent, and more preferably a yield of at least 30 percents based on the amount of 2,3-dihaloperfluoropropionyl fluoride fed to the reaction system, be obtained.

Completion of addition of the 2,3-dihaloperfluoropropionyl fluoride to the 3-haloperfluoropropene oxide in the concluding portion of Phase One to give a 2-(2',3'-dihaloperfluoropropoxy)-3-haloperfluoropropionyl fluoride is indicated when the reaction ceases to generate heat. The reaction mixture is then allowed to attain ambient temperature, or the vessel may be heated and evacuated by vacuum flashing, and the 2-(2',3'-dihaloperfluoropropoxy)-3-haloperfluoropropionyl fluoride product can be recovered by distillation.

In several exemplary runs, the concluding portion of Phase One is performed to prepare a 2-(2',3'-dihaloperfluoropropoxy)-3-haloperfluoropropionyl fluoride, as follows: Dry potassium fluoride is added to an inert, liquid reaction medium. Distilled 2,3dichloroperfluoropropionyl fluoride (>99 percent pure) is added dropwise to the mixture with stirring at 15°–20° C. The mixture is cooled to 4° C. Into the mixture is bubbled 3-chloroperfluoropropene oxide at over 3 hours. The mixture is allowed to warm to room temperature and is distilled under vacuum to collect the volatile products in a receiver cooled with a dry ice-acetone mixture. Gas chromatographic analysis of the distillate indicates the percentage yield of 2-(2',3'-dichloroperfluoropropoxy)-3-chloroperfluoropropionyl fluoride (the coupled product) and 2-(3'-chloroperfluoropropoxy)-3-chloroperfluoropropionyl fluoride (the dimer) in the distillate. The mixture is fractionally distilled to collect the epoxide dimer at 61°–63° C./125 mm Hg and the coupled product at 78°–81° C./100 mm Hg.

The infrared red spectrum of the distillate shows a strong carbonyl absorption at 1,880 cm$^{-1}$ (COF). Its $^{19}$F nuclear magnetic resonance exhibits the FCO peak at −103.8 ppm (relative to trifluoroacetic acid), the CF$_2$Cl peaks at −19 and −7.0 ppm, the CF$_2$O peaks at +2.0 to +2 ppm, and the CF peaks at 48 and 56.7 ppm.

The amount of 2,3-dichloroperfluoropropionyl fluoride ("Acid Fluoride"), propene oxide ("Oxide") and initiator ("KF"), the type and amount of liquid reaction medium ("L.R.M."), the temperature at which the 3-chloroperfluoropropene oxide is fed into the reaction mixture, the relative percent yield, and the selectivity are shown below in Table 1 for Runs 1-A to 1-E which illustrate the concluding portion of Phase One.

TABLE 1

| Run | Acid Fluoride[1] g(mole) | Oxide[2] g(mole) | KF g(mole) | L.R.M. (ml) | Temp. °C. | Relative Yield %[3] Dimer | Relative Yield %[3] Coupled | Selectivity Coupled/Dimer |
|---|---|---|---|---|---|---|---|---|
| 1-A | 120 (0.6) | 130 (0.72) | 8.8 (0.15) | Sulfolane (120) | 18–20 | 7.7 | 61.9 | 8.0 |
| 1-B | 60 (0.3) | 65 (0.36) | 4.4 (0.075) | 3-methylsulfolane (120) | 6–10 | 4.1 | 57.9 | 14.1 |
| 1-C | 10 (0.05) | 9.2 (0.05) | 0.29 (0.005) | TGME[6] (20) | 7–12 | 14.1 | 2.4 | 0.17 |
| 1-D | 60 (0.3) | 65 (0.36) | 4.4 (0.075) | Sulfolane (96) + 3-methylsulfolane (24) | 4–8 | 3.4 | 84.2 | 24.8 |
| 1-E | 60 (0.3) | 65 (0.36) | 4.4 (0.075) | Sulfolane (96) + TGME (24) | 10–14 | 11.5 | 67.4 | 5.9 |

[1]2,3-Dichlorotrifluoropropionyl fluoride
[2]3-Chloropentafluoropropylene oxide
[3]Based on the area percentage of gas chromatogram
[4]2-(2'3'-Dichloropentafluoropropoxy)-3-chlorotrifluoropropionyl fluoride
[5]2-(3'-Chlorotrifluoropropoxy)-3-chlorotrifluoropropionyl fluoride
[6]Tetraethylene glycol dimethyl ether In steps similar to those performed for Runs 1A to 1-E above, hexafluoropropene oxide is used instead of 3-chloroperfluoropropene oxide, and a 2-(2',3'-dihaloperfluoropropoxy)-perfluoropropionyl fluoride is obtained as the product instead of a 2-(2',3'-dihaloperfluoropropoxy)-3-haloperfluoropropionyl fluoride.

In Phase Two, an ether of Formula II where n=0 is prepared by decarboxylating a 2-(2',3'-dihaloperfluoropropoxy)-3-haloperfluoropropionyl fluoride in the presence of sodium carbonate or other substance which will generate a carboxylate ion at the carbonyl carbon and act as a scavenger for the eliminated fluoride ions. Representative examples of other such decarboxylating agents are the oxygen-containing salts of an alkali or alkaline earth metal, particularly a salt of a monovalent alkali metal. Suitable oxygen-containing salts include the carbonates, sulfates, sulfites, phosphates, phosphites, nitrates, nitrites, silicates, and the like, representative examples of which include bases such as potassium carbonate and sodium bicarbonate.

The decarboxylation is accomplished by adding the 2-(2',3'-dihaloperfluoropropoxy)-3-haloperfluoropropionyl fluoride dropwise to a reaction mixture in which a decarboxylating agent such as sodium carbonate is slurried with an inert liquid reaction medium, such as that described above with reference to the preliminary portion of Phase One. The 2-(2',3'-dihaloperfluoropropoxy)-3-haloperfluoropropionyl fluoride is added to the reaction mixture at a rate of about 0.1 mole per hour to about 1 mole per hour while the reaction mixture is kept at a temperature of about 45° C. to about 65° C. and is vigorously agitated. After completion of addition of the 2-(2',3'-dihaloperfluoropropoxy)-3-haloperfluoropropionyl fluoride, the mixture is stirred for an additional period of about 0.5 hours to about 3 hours at a temperature of about 50° C. to about 90° C. The reaction may be run at atmospheric pressure, or may be run in a closed system or under vacuum, at a pressure of about 0.1 MPa to about 1 MPa.

A decarboxylating agent is used in the decarboxylation reaction in an amount of about 0.9 moles to about 1.3 moles per mole of 2-(2',3'-dihaloperfluoropropoxy)-3-haloperfluoropropionyl fluoride. The liquid reaction medium may be present in the reaction mixture in an amount of about 5 moles to about 50 moles per mole of decarboxylating agent. Any level of yield of the 2,3-dihaloperfluoropropyl perfluorovinyl ether product is acceptable, but it is preferred that a yield of at least about 10 percent, and more preferably a yield of at least about 30 percent, based on the amount of 2-(2',3'-dihaloperfluoropropoxy)-3-haloperfluoropropionyl fluoride fed to the reaction system, be obtained.

If the halo atom on the pendant methyl group ("E" in the ether of Formula Ia) is fluorine, the decarboxylation is preferably run in vapor phase at a temperature in excess of 200° C. using the same decarboxylating agents as described above.

Completion of decarboxylation of a 2-(2',3'-dihaloperfluoropropoxy)-3-haloperfluoropropionyl fluoride to give a 2,3-dihaloperfluoropropyl perfluorovinyl ether in Phase Two is indicated when the reaction ceases to generate heat. The reaction mixture is allowed to attain ambient temperature, and, with heating, the vessel is then evacuated by vacuum flashing and the 2,3-dihaloperfluoropropyl perfluorovinyl ether product is recovered by distillation. This product, an ether of Formula II where n=0, may be generally represented by the formula

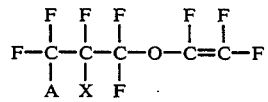

where A and X are as set forth above.

In several exemplary runs, Phase Two is performed to prepare a 2,3-dihaloperfluoropropyl perfluorovinyl ether, as follows: 2-(2',3'-dichloroperfluoropropoxy)-3-chloroperfluoropropionyl fluoride is added dropwise to sodium carbonate slurried in dry sulfolane over 2 hours with vigorous mechanical agitation. After addition of the acid fluoride is complete, the mixture is stirred for 2 hours until gas evolution has ceased (ultrasonic radiation is used in Run 2-C instead of mechanical stirring). After cooling to room temperature, the mixture is vacuum-distilled to collect volatile products in a receiver cooled with a dry ice-acetone mixture.

Gas chromatographic analysis of the distillate indicates the percent yield of 2,3-dichloroperfluoropropyl perfluorovinyl ether ("DCPVE"). Fractional distillation collects DCPVE at 54°–55° C./150 mm Hg. The infrared spectrum of the distilled product shows the $CF_2=CF$ stretching absorption at 1,840 cm$^{-1}$, indicating complete decarboxylation of the acid fluoride group. $^{19}F$ nuclear magnetic resonance exhibits a quartet at 39 ppm (relative to trifluoroacetic acid), a quartet at 45 ppm due to the $=CF_2$ group, and a triplet of a quartet at 58 ppm due to the $=CF$ group.

The amount of 2-(2',3'-dichloroperfluoropropoxy)-3-chloroperfluoropropionyl fluoride ("Acid Fluoride"), the amount of $Na_2CO_3$, the amount of sulfolane, the respective temperatures at which the acid fluoride is added to the reaction mixture and the temperature at which it is stirred after completion of addition, the mass of the distillate, the relative yield of the vinyl ether and the acid fluoride, and the percent yield are shown below in Table 2 for Runs 2-A to 2-C, which illustrate Phase Two.

TABLE 2

| Run | Acid Fluoride[1] g(mole) | $Na_2CO_3$ g(mole) | Sulfolane (ml) | Temp.[2] °C. | Distillate g | Relative Yield %[3] | | Yield[4] % |
|---|---|---|---|---|---|---|---|---|
| | | | | | | Vinyl Ether | Acid Fluoride | |
| 2-A | 370 (0.97) | 123 (1.16) | 700 | 50,81 | 290 | 90.0 | 5.8 | 98.1 |
| 2-B | 145 (0.38) | 48.3 (0.46) | 250 | 70,85 | 59 | 80.6 | — | 41.9 |
| 2-C | 30.4 (0.08) | 10 (0.096) | 60 | 50,80 | 20 | 94.2 | 2.4 | 78.8 |

[1]2-(2',3'-Dichloropentafluoropropoxy)-3-chlorotrifluoropropionyl fluoride
[2]Addition temperature on the left column and heating temperature after addition on the right column
[3]Area percentage in gas chromatogram
[4]Yield of 2,3-dichloropentafluoropropyl trifluorovinyl ether An ether of Formula III where n=0 (a 3-oxaperfluorohexa-1,5-diene) is prepared in Phase Three by the dehalogenation of a 2,3-dihaloperfluoropropyl perfluorovinyl ether, using for example a metal dehalogenating agent such as zinc powder or magnesium. This is performed in an inert liquid reaction medium such as 1-methyl-2-pyrrolidinone, N,N-dimethylformamide, dimethylsulfoxide or N,N-dimethylacetamide. 2,3-Dihaloperfluoropropyl perfluorovinyl ether is added dropwise to a reaction vessel containing the dehalogenating agent dispersed in the inert liquid reaction medium. 2,3-Dihaloperfluoropropyl perfluorovinyl ether is added to the reaction mixture at a rate of about 0.5 moles to about 5 moles per hour while the reaction mixture is kept at a temperature of about 25° C. to about 60° C. and is vigorously agitated, for example with ultrasonic irradiation. After completion of addition of the 2,3-dihaloperfluoropropyl perfluorovinyl ether, the mixture is vigorously agitated for an additional period of about 0.5 hours to about 2 hours at a temperature of about 25° C. to about 50° C.

The reaction may be run at atmospheric pressure, or may be run in a closed system or under vacuum, at a pressure of about 0.1 MPa to about 1 MPa. Any level of yield of the perfluoroallylvinyl ether product (pentafluoro-2-propenyl perfluorovinyl ether) is acceptable, but it is preferred that a yield of at least about 10 percent, and more preferably a yield of at least about 20 percent, based on the amount of 2,3-dihaloperfluoropropyl perfluorovinyl ether fed to the reaction system, be obtained.

The dehalogenating agent is used in the dehalogenation reaction in an amount of about 2 g-atoms (moles) to about 2.5 g-atoms (moles) per mole of 2,3-dihaloperfluoropropyl perfluorovinyl ether. The liquid reaction medium may be present in an amount of about 2 moles to about 20 moles per mole of dehalogenating agent.

products contained in the volatile distillate is determined by gas chromatographic analysis.

The volatile product is fractionally distilled to collect perfluoro-2-propenyl perfluorovinyl ether at 44°–45° C. at atmospheric pressure: Infrared analysis shows 1,840 cm$^{-1}$ (C=C of vinyl group), 1,795 cm$^{-1}$(C=C of allyl group). $^{19}$F nuclear magnetic resonance analysis shows (ppm from CF$_3$CO$_2$H), 1.5 ppm (CF$_2$, multiple), 19.8 ppm (CF$_2$=of allyl group, triplet of quartet), 38.0 ppm (CF$_2$=of vinyl group, doublet of doublet), 60.4 ppm (CF$_2$=of vinyl group, triplet of quartet), 137.4 ppm (CF=of allyl group, triplet of quartet).

The amount of 2,3-dichloroperfluoropropylvinyl ether ("DCPVE") and zinc, the type and amount of liquid reaction medium ("L.R.M."), the amount of recovered DCPVE, perfluoro-2-propenyl perfluorovinyl ether product (perfluoroallylvinyl ether, "PAVE"), the amount of byproducts, and the percent yield of PAVE are shown below in Table 3 for Runs 3-A to 3-H which illustrate Phase Three.

TABLE 3

| Run | DCPVE$^1$ g(mole) | Zn g(g-atom) | L.R.M. (ml) | g | DCPVE$^1$ | PAVE$^2$ | Other | Yield of PAVE$^2$, % |
|---|---|---|---|---|---|---|---|---|
| 3-A | 60 (0.2) | 26.2 (0.4) | 1-methyl-2-pyrrolidinone (220) | 34 | 15.4 | 79.9 | 4.5 | 65.1 |
| 3-B | 15 (0.05) | 6.5 (0.1) | Dimethylformamide (100) | 1.5 | 5.9 | 85.9 | 12.4 | 15.1 |
| 3-C | 3 (0.01) | 1.3 (0.02) | Dimethylsulfoxide (25) | 0.7 | 58.5 | 36.2 | 1.9 | 26.8 |
| 3-D | 3 (0.01) | 1.3 (0.02) | Tetraethylene glycol dimethyl ether (25) | 0.2 | 81.7 | 9.6 | 5.2 | 4.6 |
| 3-E | 3 (0.01) | 1.3 (0.02) | Sulfolane (20) + 3-Methylsulfolane (4) | 2.2 | 81.5 | 7.5 | 10.1 | 39.1 |
| 3-F | 3 (0.01) | 1.3 (0.02) | Dimethylacetamide (25) | 1.5 | 60.3 | 35.7 | 2.1 | 59.2 |
| 3-G | 3 (0.01) | 1.3 (0.02) | 2-Pyrrolidinone (25) | 1.9 | 51.1 | 41.4 | 5.2 | 70.5 |
| 3-H | 3 (0.01) | 1.3 (0.02) | Formamide (25) | 1.3 | 95.0 | 4.2 | — | 47.8 |

$^1$DCPVE = 2,3-Dichlorotrifluoropropyl Trifluorovinyl Ether
$^2$PAVE = Trifluorovinyl Pentafluoroallyl Ether A greater yield of an ether of Formula III where n=0 will be obtained if the halogen atom at the 3-position of the 2,3-dihaloperfluoropropyl perfluorovinyl ether ("A" in the ether of Formula IIa) is chlorine, bromine or iodine rather than fluorine.

Completion of the dehalogenation of the 2,3-dihaloperfluoropropyl perfluorovinyl ether is indicated when the reaction ceases to generate heat. The vessel is then heated and evacuated by vacuum flashing and the pentafluoro-2-propenyl perfluorovinyl ether product is recovered by distillation. The pentafluoro-2-propenyl perfluorovinyl ether product (an ether of Formula III where n=0) may be generally represented by the formula

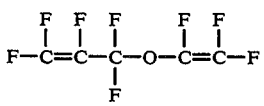

IIIa

In several exemplary runs, Phase Three is performed to prepare a pentafluoro-2-propenyl perfluorovinyl ether, as follows: 2,3-dichloroperfluoropropylvinyl ether ("DCPVE") is added dropwise at 30°–50° C. to a mixture of zinc powder and a dry, inert liquid reaction medium, and such reaction mixture is irradiated with an ultrasonic wave. After addition of the vinyl ether over 60 minutes is complete, the mixture is agitated further by ultrasonic irradiation, and it is then flash-distilled under vacuum to collect the volatile products in a dry ice-acetone cooled receiver. The percentage of pentafluoro-2-propenyl perfluorovinyl ether, unreacted 2,3-dichloroperfluoropropylvinyl ether, and other by- An ether of Formula I where n=1 is prepared in Phase Four from an ether of Formula Ia, a 2-(2′,3′-dihaloperfluoropropoxy)-3-haloperfluoropropionyl fluoride. This is accomplished by forming a slurry of an alkali metal fluoride (MF) in an inert liquid reaction medium and reacting the 2-(2′,3′-dihaloperfluoropropoxy)-3-haloperfluoropropionyl fluoride with a 3-haloperfluoropropene oxide therein. The fluoride ion produces a stable alkoxide ion at the carbonyl carbon of the 2-(2′,3′-dihaloperfluoropropoxy)-3-haloperfluoropropionyl fluoride. This alkoxide ion opens the oxirane ring at the 2-carbon of the 3-haloperfluoropropene oxide to generate a carbonyl group in a manner similar to that by which a 2-(2′,3′-dihaloperfluoropropoxy)-3-haloperfluoropropionyl fluoride is itself produced from 3-haloperfluoropropene oxide in the concluding portion of Phase One. Occurrence of the desired addition of the alkoxide ion at the 2-carbon of the 3-haloperfluoropropene oxide couples the carbonyl fluoride and the propene oxide, and provides a second ether functionality in the molecule in addition to regenerating a carbonyl fluoride. Phase Four in the processes of this invention yields a 2-[2′-(2″,3″-dihaloperfluoropropoxy)-3′-haloperfluoropropoxy]-3-haloperfluoropropionyl fluoride, which can be generally represented by a formula such as

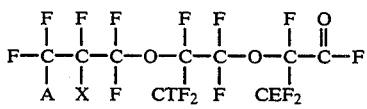

Ib where A, T, E and X are as set forth above.

To prepare a 2-[2'-(2'',3''-dihaloperfluoropropoxy)-3'-haloperfluoropropoxy]-3-haloperfluoropropionyl fluoride, addition of propene oxide to the reaction mixture is made at a rate of about 0.2 moles per hour to about 2 moles per hour. While maintaining a temperature of about −10° C. to about 25° C., 3-haloperfluoropropene oxide is added to the reaction mixture in an amount of about 0.9 moles to about 1.3 moles per mole of a 2-(2',3'-dihaloperfluoropropoxy)-3-haloperfluoropropionyl fluoride, as produced for example in the concluding portion of Phase One. The additional charge of alkali metal fluoride is made to the reaction mixture in an amount of about 0.01 moles to about 0.3 moles per mole of 2-(2',3'-dihaloperfluoropropoxy)-3-haloperfluoropropionyl fluoride. A liquid reaction medium, as described above with relation to the preliminary portion of Phase One, may be present in an amount of about 2 moles to about 10 moles per mole of 2-(2',3'-dihaloperfluoropropoxy)-3-haloperfluoropropionyl fluoride.

The reaction may be run at atmospheric pressure, or may be run in a closed system or under vacuum, at a pressure of about 0.1 MPa to about ]MPa. Any level of yield of the 2-[2'-(2'',3''-dihaloperfluoropropoxy)- 3'-haloperfluoropropoxy]-3-haloperfluoropropionyl fluoride product is acceptabler but it is preferred that a yield of at least about 10 percent, and more preferably a yield of at least about 20 percent, based on the amount of 2-(2',3'-dihaloperfluoropropoxy)-3-haloperfluoropropionyl fluoride fed to the reaction system, be obtained.

Completion of addition of the 2-(2',3'-dihaloperfluoropropoxy)-3-haloperfluoropropionyl fluoride to the 3-haloperfluoropropene oxide in Phase Four to give a 2-[2'-(2'',3''-dihaloperfluoropropoxy)-3'-haloperfluoropropoxy]-3-haloperfluoropropionyl fluoride is indicated when the reaction ceases to generate heat. The reaction mixture is then allowed to attain ambient temperature, or it may be heated, and the vessel can then be evacuated by vacuum flashing and the 2-[2'-(2'',3''-dihaloperfluoropropoxy)-3'-haloperfluoropropoxy]-3-haloperfluoropropionyl fluoride product can be recovered by distillation.

3-haloperfluoropropene oxide. Ethers containing such multiple ether functionalites are polyethers of Formula I where n=2 to 6.

In several exemplary runs, Phase Four is performed to prepare a 2-[2'-(2'',3''-dihaloperfluoropropoxy)-3'-haloperfluoropropoxy]-3-haloperfluoropropionyl fluoride, as follows: Dry alkali fluoride is slurried in an inert liquid reaction medium at ambient temperature with stirring. Distilled 2-(2',3'-dichloropentafluoropropoxy)-tetrafluoropropionyl fluoride is added dropwise to the mixture at ambient temperature with stirring. 3-Chloropentafluoropropene oxide is bubbled into the stirred reaction mixture over 4 hours. The reaction mixture is stirred at room temperature (23.5°–26° C.) overnight and is then transferred to a separatory funnel. The heavy layer is separated. Gas chromatographic analysis of the heavy layer indicates the percentage yield therein of 2-[2'-(2'',3''-dichloropentafluoropropoxy)-hexafluoropropoxy)]-3-chlrotrifluoroporopionyl fluoride (product) and 2-(2',3'-dichloropentafluoropropoxy)tetrafluoropropionyl fluoride (unconverted starting material).

Fractional distillation under vacuum yields 2-[2'-(2'',3''-dichloropentafluoropropoxy)hexafluoropropoxy)]-3-chlorotrifluoropropionyl fluoride at 86° C./28 mmHg. Infrared analysis of the heavy layer shows 1,880 cm$^{-1}$ (COF). $^{19}$F nuclear magnetic resonance analysis shows (ppm from CF$_3$CO$_2$H), −104.3 ppm (COF), −13.2 ppm (CF$_2$Cl), −9.5 ppm (CF$_2$Cl), −8.2 ppm (CF$_3$), −4.0 ppm (CF$_2$O), 47.5 ppm (CFCl), 55.0 ppm (CFCl), 66.7 ppm (CFO).

The amount of 2-(2',3'-dichloropentafluoropropoxy)-tetrafluoropropionyl fluoride ("AF-1"), propene oxide ("Oxide") and alkali metal fluoride ("MF"), the type and amount of liquid reaction medium ("L.R.M."), the temperature at which the propene oxide is bubbled into the reaction mixture, the mass of the product obtained (AF-2=2-[2'-(2'',3''-dichloropentafluoropropoxy)hexafluoropropoxy)] -3chlrotrifluoroporopionyl fluoride), and the relative percent yield are shown below in Table 4 for Runs 4-A to 4-G which illustrate Phase Four.

TABLE 4

| Run | AF-1[1] g(mole) | Oxide[2] g(mole) | MF g(mole | L.R.M.[3] (ml) | Temp. °C. | g | Product[4] AF-2 | AF-1 | g | Yield[5] % |
|---|---|---|---|---|---|---|---|---|---|---|
| 4-A | 18 (0.05) | 12.7 (0.06) 1.5 (0.01) | CsF (20) | TGME | 4–10 | 11 | 58.9 | 38.1 | — | 31.1 |
| 4-B | 24.5 (0.068) | 15 (0.075) 2.07 (0.0136) | CsF (20) | TGME | 20–40 | 40 | 68.5 | 22.4 | — | >100[6] |
| 4-C | 18 (0.05) | 12.7 (0.06) 0.026 (0.01) | LiF (20) | TGME | 20–35 | 16 | 3.6 | 93.8 | — | 1.3 |
| 4-D | 27 (0.075) | 17 (0.09) 2.25 (0.015) 0.264 (0.0015) | CsF (30) | TGME +18-Crown-6 | 20–40 | 44 | 59.0 | 2.6 | — | >100[6] |
| 4-E | 36 (0.1) | 30 (0.16) 3 (0.02) | CsF (40) | TGME | 25–45 | 85 | 53.8 | 33.4 | — | >100[6] |
| 4-F | 125 (0.347) | 104 (0.55) 10.5 (0.07) | CsF (130) | TGME | 45–65 | 217 | 44.4 | 44.1 | — | >100[6] |
| 4-G | 160 (0.44) | 125 (0.66) 1.32 (0.088) | CsF (170) | TGMe | 25–40 | 204 | 47.5 | 33.5 | 113[7] | 71.1 |

[1]AF-1 = 2-(2',3-Dichloropentafluoropropoxy)tetrafluoropropionyl fluoride.
[2]Oxide = 3-chloropentafluoropropene oxide.
[3]SF = Sulfolane; MSF = 3-Methylsulfolane; TGME = Tetraethylene glycol dimethyl ether.
[4]g: Weight of product separated by separating funnel; %: Area percent in gas chromatogram.
[5]Percent yield based on reacted AF-1 using GC area percent.
[6]Yield exceeds 100% because separated product before distillation contains the solvent and the metal fluoride.
[7]Isolated yield after fractional distillation.

By successive repetition of the steps used to prepare an ether of Formula Ib, as set forth above, a six-membered, or greater, polyether can be prepared by continued conversion of the terminal carbonyl carbon to an alkoxide ion and addition of it to another equivalent of In Phase Five of the processes of this invention, an ether of Formula II where n=1 is prepared by decarboxylating a 2-[2'-(2'',3''-dihaloperfluoropropoxy)-3'-haloperfluoropropoxy]-3-haloperfluoropropionyl fluoride in the presence of sodium carbonate or another substance which will generate a carboxylate ion at the carbonyl carbon and act as a scavenger for the eliminated fluoride ions. Representative examples of other such decarboxylating agents are the oxygen-containing salts of an alkali or alkaline earth metal, particularly a salt of a monovalent alkali metal. Suitable oxygen-containing salts include the carbonates, sulfates, sulfites, phosphates, phosphites, nitrates, nitrites, silicates, and the like, representative examples of which include bases such as potassium carbonate and sodium bicarbonate.

This decarboxylation is accomplished by adding the 2-[2'-(2'',3''-dihaloperfluoropropoxy)-3'-haloperfluoropropoxy]-3-haloperfluoropropionyl fluoride dropwise to a reaction mixture in which a decarboxylating agent such as sodium carbonate is slurried with an inert liquid reaction medium, such as that described above with reference to the preliminary portion of Phase One. The 2-[2'-(2'',3''-dihaloperfluoropropoxy)-3'-haloperfluoropropoxy]-3-haloperfluoropropionyl fluoride is added to the reaction mixture at a rate of about 0.1 mole per hour to about 1 mole per hour while the reaction mixture is kept at a temperature of about 45° C. to about 65° C. and is vigorously agitated. After completion of addition of the 2-[2'-(2'',3''-dihaloperfluoropropoxy)-3'-haloperfluoropropoxy]-3-haloperfluoropropionyl fluoride, the mixture is stirred for an additional period of about 0.5 hours to about 3 hours at a temperature of about 50° C. to about 90° C. The reaction may be run at atmospheric pressure, or may be run in a closed system or under vacuum, at a pressure of about 0.1 MPa to about 1 MPa.

A decarboxylating agent such as sodium carbonate is used in the decarboxylation reaction in an amount of about 0.9 moles to about 1.3 moles per mole of 2-[2'-(2'',3''-dihaloperfluoropropoxy)-3'-haloperfluoropropoxy]-3-haloperfluoropropionyl fluoride. The liquid reaction medium may be present in the reaction mixture in an amount of about 5 moles to about 50 moles per mole of decarboxylating agent. Any level of yield of the 3,6-dioxa-5-halodifluoromethyl-8,9-dihaloperfluoro-1-nonene product is acceptable, but it is preferred that a yield of at least about 10 percent, and more preferably a yield of at least about 30 percent, based on the amount of 2-[2'-(2'',3''-dihaloperfluoropropoxy)-3'-haloperfluoropropoxy]-3-haloperfluoropropionyl fluoride fed to the reaction system, be obtained. If the halo atom on the pendant methyl group ("E" in the ether of Formula Ib) is fluorine, the decarboxylation is preferably run in vapor phase at a temperature in excess of 200° C. using the same decarboxylating agents as described above.

Completion of decarboxylation of a 2-[2'-(2'',3''-dihaloperfluoropropoxy)-3'-haloperfluoropropoxy]-3-haloperfluoropropionyl fluoride to give a 3,6-dioxa-5-halodifluoromethyl-8,9-dihaloperfluoro-1-nonene in Phase Five is indicated when the reaction ceases to generate heat. The reaction mixture is allowed to attain ambient temperature, and, with heating, the vessel is then evacuated by vacuum flashing and the 3,6-dioxa-5-halodifluoromethyl-8,9-dihaloperfluoro-1-nonene product is recovered by distillation. This product, an ether of Formula II where n=1, may be generally represented by the formula

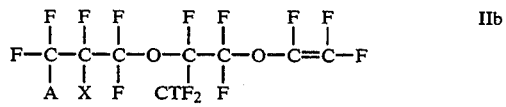

where A, T and X are as set forth above. A polyether of Formula II where n=2 to 6 may be prepared by performing a decarboxylation, as described above, on the corresponding polyether of Formula I.

In several exemplary runs, Phase Five is performed to prepare a 3,6-dioxa-5-halodifluoromethyl-8,9-dihaloperfluoro-1-nonene, as follows: Distilled 2-[2'-(2'',3''-dichloropentafluoropropoxy)hexafluoropropoxy]-3-chlorotrifluoropropionyl fluoride is added dropwise to sodium carbonate slurried in sulfolane at 45°–52° C. with vigorous stirring. The mixture is stirred vigorously and is heated to 80°–81° C. until the evolution of carbon dioxide has ceased. After cooling to ambient temperature, the reaction mixture is distilled under vacuum to collect the volatile products in a receiver cooled with a dry ice-acetone mixture. Gas chromatographic analysis of the distillate indicates the percentage yield therein of the 3,6-dioxa-5-trifluoromethyl-8,9-dichloroperfluoro-1-nonene product [referred to in Table 5 as 2-(2',3'-dichloropentafluoropropoxy)hexafluoropropyl trifluorovinyl ether or "FVE"], and of 2-[2'-(2'',3''-dichloropentafluoropropoxy)hexafluoropropoxy]-3-chlorotrifluoropropionyl fluoride (unreacted starting material).

The distillate is fractionally distilled to collect 3,6-dioxa-5-trifluoromethyl-8,9-dichloroperfluoro-1-nonene at 58° C./24 mmHg. The infrared spectrum of the distilled product shows the trifluorovinyl stretching vibration at 1,840 cm$^{-1}$, indicating the elimination of the acid fluoride group and the formation of the trifluorovinyl group. The presence of the trifluorovinyl group is confirmed by $^{19}$F nuclear magnetic resonance analysis, which exhibits a doublet of doublet due to CF$_2$=at 26.5 ppm, a triplet of quartet due to CF$_2$=at 33.5 ppm and a triplet of quartet due to CF at 47.7 ppm (relative to CF$_3$CO$_2$H).

The amount of 2-[2'-(2'',3''-dichloropentafluoropropoxy)hexafluoropropoxy)]-3-chlorotrifluoropropionyl fluoride ("AF-2"), amount of Na$_2$CO$_3$, amount of sulfolane, the respective temperatures at which the AF-2 is added to the reaction mixture and at which the reaction mixture is stirred, the mass of the distillate, the relative yield, and the percent yield are shown below in Table 5 for Runs 5-A and 5-B, which illustrate Phase Five.

TABLE 5

| Run | AF-2[1] g(mole) | Na$_2$CO$_3$ g(mole) | Sulfolane (ml) | Temp.[2] °C. | g | Product[3] (%) FVE | AF-2 | Yield[4] % |
|---|---|---|---|---|---|---|---|---|
| 5-A | 55 (0.1) | 12.7 (0.12) | 70 | 50,80 | 43 | 93.4 | 4.4 | 89.1 |

TABLE 5-continued

| Run | AF-2[1] g(mole) | Na₂CO₃ g(mole) | Sulfolane (ml) | Temp.[2] °C. | g | Product[3] (%) FVE | AF-2 | Yield[4] % |
|---|---|---|---|---|---|---|---|---|
| 5-B | 176 (0.32) | 37.3 (0.38) | 200 | 50,81 | 124 | 97.8 | 1.1 | 81.8 |

[1]AF-2 = 2-(2'-(2'',3''-dichloropentafluoropropoxy)hexafluoropropoxy)-3-chlorotrifluoropropionyl fluoride.
[2]Addition temperature on the left column and heating temperature after addition on the right column.
[3]g = Weight of crude distillate.
FVE = 2-(2',3'-dichloropentafluoropropoxy)hexafluoropropyl trifluorovinyl ether.
AF-2 = 2-(2'-2'',3''-dichloropentafluoropropoxyhexa)fluoropropoxy)-3-chlorotrifluoropropionyl fluoride.
[4]Yield of 2-(2',3'-dichloropentafluoropropoxy)hexafluoropropyl trifluorovinyl ether.

An ether of Formula III where n=1 is prepared in Phase Six by the dehalogenation of a 3,6-dioxa-5-halodifluoromethyl-8,9-dihaloperfluoro-1-nonene using for example a metal dehalogenating agent such as zinc powder or magnesium. This is performed in an inert liquid reaction medium such as 1-methyl-2-pyrrolidinone, N,N-dimethylformamide, dimethylsulfoxide or N,N-dimethylacetamide. 3,6-dioxa-5-halodifluoromethyl-8,9-dihaloperfluoro-1-nonene is added dropwise to a reaction vessel containing the dehalogenating agent dispersed in the inert liquid reaction medium. 3,6-Dioxa-5-halodifluoromethyl-8,9-dihaloperfluoro-1-nonene is added to the reaction mixture at a rate of about 0.5 moles to about 5 moles per hour while the reaction mixture is kept at a temperature of about 25° C. to about 60° C. and is agitated vigorously, for example with ultrasonic irradiation. After completion of addition of the 3,6-dioxa-5-halodifluoromethyl-8,9-dihaloperfluoro-1-nonene, the mixture is agitated vigorously for an additional period of about 0.5 hours to about 2 hours at a temperature of about 25° C. to about 50° C. The reaction may be run at atmospheric pressure, or may be run in a closed system or under vacuum, at a pressure of about 0.1 MPa to about 1 MPa.

The dehalogenating agent is used in the dehalogenation reaction in an amount of about 2 g-atoms (moles) to about 2.5 g-atoms (moles) per mole of 3,6-dioxa-5-halodifluoromethyl-8,9-dihaloperfluoro-1-nonene. The liquid reaction medium may be present in an amount of about 2 moles to about 20 moles per mole of dehalogenating agent. Any level of yield of the 3,6-dioxa-5-halodifluoromethylperfluoronona-1,8-diene product is acceptable, but is is preferred that a yield of at least about 5 percent, and more preferably a yield of at least about 10 percent, based on the amount of 3,6-dioxa-5-halodifluoromethyl-8,9-dihaloperfluoro-1-nonene fed to the reaction system, be obtained.

A greater yield of an ether of Formula III where n=1 will be obtained if the halogen atom at the 9-position of the 3,6-dioxa-5-halodifluoromethyl-8,9-dihaloperfluoro-1-nonene ("A" in the ether of Formula IIb) is chlorine, bromine or iodine rather than fluorine.

Completion of the dehalogenation of the 3,5-dioxa-5-halodifluoromethyl-8,9-dihaloperfluoro-1-nonene is indicated when the reaction ceases to generate heat. The vessel is then heated and evacuated by vacuum flashing, and the 3,6-dioxa-5-halodifluoromethylperfluoronona-1,8-diene product is recovered by distillation. The 3,6-dioxa-5-halodifluoromethylperfluoronona-1,8-diene product may be generally represented by the formula

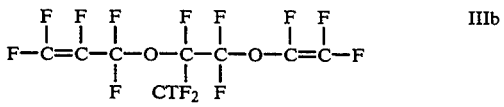

where T is as set forth above. A polyether of Formula III where n=2 to 6 can be prepared by performing a dehalogenation, as described above, on a corresponding polyether of Formula II.

In several exemplary runs, Phase Six is performed to prepare a 3,6-dioxa-5-halodifluoromethylperfluoronona-1,8-diene, as follows: Zinc dust is covered with a dry, inert liquid reaction medium and the reaction mixture is irradiated with an ultrasonic wave. To the dispersed mixture is added dropwise distilled 3,6-dioxa-5-trifluoromethyl-8,9-dichloroperfluoro-1-nonene over 1 hour at 32°–48° C. The red colored reaction mixture is distilled under vacuum at ambient temperature to collect volatile products in a receiver cooled with dry ice-acetone. Gas chromatographic analysis indicates the percentage of the 3,6-dioxa-5-trifluoromethylperfluoronona-1,8-diene product ("PAVE-I", also referred to as 2-(2'-pentafluoropro-penyloxy)hexafluoropropyl trifluorovinyl ether in Table 6) and 3,6-dioxa-5-trifluoromethyl-8,9-dichloroperfluoro-1-nonene ("FVE", unreacted starting material) in the distillate.

The condensate is fractionally distilled at 61° C./97 mmHg to isolate PAVE-1. Infrared analysis of PAVE-1 shows two C=C stretching absorptions at 1,820 cm⁻¹ due to the trifluorovinyl group, and at 1,800 cm⁻¹ due to the pentafluoroallyl group. ¹⁹F nuclear magnetic resonance analysis of PAVE-1 exhibits (ppm from CF₃CO₂) −6.9 ppm (OCF₂, m), 4.4 ppm (CF₃, m), 8.2 ppm (OCF₂, m), 18.4 ppm (CF₂=of perfluoroallyl group, triplet of quartet), 30.1 ppm (CF₂=of perfluoroallyl group, triplet of quartet), 40.0 ppm (CF₂=of perfluorovinyl group, doublet of doublet), 47.4 ppm (CF₂=of perfluorovinyl group, triplet of quartet), 60.4 ppm (CF=of perfluorovinyl group, triplet of quartet), 71.0 ppm (CFO, triplet), and 114.8 ppm (CF=of perfluoroallyl group, triplet of quartet).

The amount of 3,6-dioxa-5-trifluoromethyl-8,9-dichloroperfluoro-1-nonene ("FVE") and zinc, the type and amount of liquid reaction medium ("L.R.M."), the mass of the product, the relative yield of the 3,6-dioxa-5-trifluoromethylperfluoronona-1,8-diene ("PAVE-]") product and the 3,6-dioxa-5-trifluoromethyl-8,9-dichloroperfluoro-1-nonene ("FVE") unreacted starting material, and the percent yield of PAVE-1 are shown below in Table 6 for Runs 6-A to 6-H which illustrate Phase Six.

TABLE 6

| Run | FVE[1] g | Zn[2] (g) | L.R.M.[3] (ml) | g | Product[4] (%) PAVE-1 | FVE | Yield[5] % |
|---|---|---|---|---|---|---|---|
| 6-A | 4.65 | dust (1.3) | MPY (25) | 2.4 | 24.8 | 7.23 | 24.1 |
| 6-B | 25 | dust (29) | MPY (160) | 9.5 | 31.1 | 52.9 | 17.5 |
| 6-C | 4.65 | dust (1.3) | SF (20) | 3.3 | 0.9 | 99.1 | 2.5 |
| 6-D | 4.65 | dust (1.3) | DMF (25) | 2.2 | 29.3 | 67.9 | 24.1 |
| 6-E | 4.65 | dust (1.3) | TGME (25) | 3.0 | 17.0 | 80.2 | 26.8 |
| 6-F | 4.65 | dust (2.6) | DMSO (25) | 1 | 1.7 | 0.7 | — |
| 6-G | 4.65 | dust (3.78) | ACPY (25) | — | 7.9 | 19.6 | — |
| 6-H | 3.3 | dust (2.5) | ACCL | 1.6 | 22.3 | 72.8 | 19.7 |

[1]FVE = 2-(2',3'-dichloropentafluoropropoxy)hexafluoropropyl trifluorovinyl ether.
[2]Zinc dust of 7u (micron) in particle size from Alfa Chemicals.
[3]MPY = 1-Methyl-2-pyrrolidinone.
TGME = Tetraethylene glycol dimethyl ether.
DMSO = Dimethylsulfoxide.
ACCL = 1-Acetylcaprolactam.
FTBA = Perfluorotributylamine.
DMF = Dimethylformamide.
SF = Sulfolane.
HMPA = Hexamethylphosphoramide.
BCN = Benzlycyanide.
FTDP = Perfluorotetradecaphenanthrene.
ACPY = 1-Acetyl-2-pyrrolidinone.
[4]g = Weight of crude distillate. Area percent of gas chromatogram for 2-(2'-pentafluoropropenyloxy)-hexafluoropropyl trifluorovinyl ether, PAVE-1 and FVE.
[5]Yield of PAVE-1 based on area percent and weight of the distillate.

All manipulations described above are performed under nitrogen to exclude air and moisture. Boiling points reported are uncorrected. Reagents other than 3-chloropentafluoropropene oxide are dried before use; inorganic salts are dried in a vacuum oven and weighed in a dry box, solvents are dried over a zeolite molecular sieve under nitrogen atmosphere.

An ether, diether or polyether having vinyl or allyl unsaturation, or both, such as a perfluorovinylallyl ether, a 3,6-dioxa-5-halodifluoromethylperfluoronona-1,8-diene, or a polyether described Formula II or III where n=2 to 6 can be polymerized with one or more ethylenically unsaturated monomers such as tetrafluoroethylene, 2-perfluorovinyloxyethanesulfonyl fluoride, 2-chlorotetrafluoroethyl trifluorovinyl ether, or 2-fluorosulfonyltetrafluoroethyl trifluorovinyl ether, to prepare a thermoplastic, melt processible polymer. The use of a perfluoroallylvinyl ether, a 3,6-dioxa-5-halodifluoromethylperfluoronona-1,8-diene or a similarly unsaturated polyether in a copolymer with an ethylenically unsaturated monomer is further described in U.S. Pat. No. 5,264,508, which is incorporated in its entirety herein.

In several exemplary runs, a perfluoroallylvinyl ether is polymerized with ethylenically unsaturated monomers as follows:

Run A. Perfluoroallylvinyl ether (25 g) and tetrafluoroethylene are separately fed into an aqueous Infrared spectra of the copolymer show no absorption at 1,800–1,850 cm$^{-1}$, but do show strong absorption at 1,155–1,365 cm$^{-1}$ for the C-F stretching and at 1,015 cm$^{-1}$ for the C-O stretching. These results suggest that the perfluoroallyl group does not remain as a pendant group on the copolymer chain. Dynamic mechanical spectroscopy of the copolymer in a 0.5 in×2 in×⅛ in molded plaque shows a sharp drop in elastic modulus at 60° C., indicating that the copolymer does not crosslink, but rather is thermoplastic.

Run B. Tetrafluoroethylene is fed into a mixture of perfluoroallylvinyl ether (17.6 g) and 2-perfluorovinyloxyethanesulfonyl fluoride (32.4 g) emulsified in water (300 ml), which mixture contains ammonium perfluorooctanoate (1.66 g), sodium dihydrogen phosphate (1.03 g), disodium monohydrogen phosphate (1.25 g), and ammonium persulfate (0.25 g) under nitrogen. The pressure and temperature of the reaction mixture are kept at 175 psi and 60° C., respectively. After 64 g of tetrafluoroethylene are introduced, the reaction mixture is cooled to ambient temperature (23°–26.5° C.) and is discharged to atmospheric pressure. Diluted hydrochloric acid (50 ml) is added to coagulate the copolymer particles, which are collected by filtration. Washing with deionized water and drying under vacuum gives colorless copolymer particles. The copolymer is titrated with caustic to give an equivalent weight of 1,137. The copolymer is readily pressed at 280° C. to give a colorless clear film.

In several exemplary runs, a 3,6-dioxa-5-halodifluoromethylperfluoronona-1,8-diene is polymerized Run C. Tetrafluoroethylene is fed into an emulsified mixture of 3,6-dioxa-5-trifluoromethylperfluoronona-1,8-diene (2.4 g), ammonium persulfate (0.16 g), ammonium perfluorooctanoate (1.66 g), sodium dihydrogen phosphate (1.03 g) and disodium monohydrogen phosphate (1.25 g) in deionized water (300 ml). The pressure and temperature of the reaction mixture are kept at 100 psi and 60° C., respectively. After 15 g of tetrafluoroethylene are introduced over 60 minutes, the reaction mixture is cooled to ambient temperature (23.5°–26° C.) and discharged to atmospheric pressure. Diluted hydrochloric acid (50 ml) is added to coagulate the polymer particles, which are collected by filtration. Washing with deionized water and methanol and drying under vacuum gives 12 g of colorless polymer particles. The infrared spectrum of the copolymer does not show the perfluorovinyl C=C double bond absorption at 1,840 cm$^{-1}$, but does show the perfluoroallyl C=C double bond absorption at 1,800 cm$^{-1}$, indicating that the perfluorovinyl group is incorporated in the main chain of the copolymer, while the perfluoroallyl group remains as a pendant, side chain.

Run D. 2-Chlorotetrafluoroethyl trifluorovinyl ether (47 g) and 3,6-dioxa-5-trifluoromethylperfluoronona-1,8-diene (5 g) are emulsified with an aqueous mixture (300 ml) of ammonium perfluorooctanoate (1.66 g), ammonium persulfate (0.32 g), sodium dihydrogen phosphate (1.03 g), and disodium monohydrogen phosphate (1.25 g). After degassing under vacuum, tetrafluoroethylene is fed into the reaction mixture, and the pressure and temperature of the mixture are maintained at 100 psi and 60° C., respectively. After 40 g of tetrafluoroethylene are introduced over 2 hours, the reaction mixture is cooled to ambient temperature (23.5°–26° C.) and is discharged to atmospheric pressure. Diluted hydrochloric acid is added to the reaction mixture to coagulate the copolymer particles, which are collected by filtration. Washing with deionized water and drying under vacuum give 55 g of colorless copolymer particles. The infrared spectrum of the terpolymer exhibits the perfluoroallyl C=C stretching band at 1,795 cm$^{-1}$. The differential scanning calorimetry of the terpolymer shows neither exothermic nor endothermic activity from ambient temperature to 350° C., indicating that the terpolymer is amorphous.

In several exemplary runs, the terpolymer prepared in Run D is cured as follows:

Run E. A mixture of the terpolymer prepared in Run D (6 g), 1,6-diiodoperfluorohexane (0.5391 g), 2,5-dimethyl-2,5-di(tert-butylperoxy)hexane (0.3361 g), and calcium hydroxide (0.31 g) is slurried in 1,1,2-trichloro-1,2,2-trifluoroethane (150 ml). The mixture is evacuated using a rotary evaporator to strip the solvent. The dry powder obtained is placed in a mold (1.25×2.5 cm$^2$) and pressed at 175° F. The preform obtained therefrom is preheated at 350° F. for 2 minutes and is precured at the same temperature by pressing at a pressure of 5 tons for 15 minutes. The precured preform is post-cured at 450° F. for 2 hours. Dynamic mechanical properties of the cured polymer are measured with a Rheometrics Mechanical Spectrometer Model 605 in the torsional rectangular mode from −175° C. to 330° C. The storage modulus, G′, of the terpolymer shows a rubbery plateau extending from a glass transition temperature at 15° C. to 340° C., which indicates crosslinking. The cured copolymer is transparent and possesses a rubbery resilience.

Run F. The terpolymer prepared in Run D (6 g) and 2,5-dimethyl-2,5-di(tert-butylperoxy)hexane (0.3356 g) are added to 1,1,2-trichloro-1,2,2-trifluoroethane (150 ml). The mixture is evacuated using a rotary evaporator to give a colorless fine powder. The polymer mixture is added to a mold (1.25×2.5 cm$^2$) and is pressed at 175° F. The preform obtained thereby is preheated at 350° F. for 2 minutes and is precured at 350° F. by pressing at a pressure of 5 tons for 15 minutes. The precured preform is post-cured at 450° F. for 2 hours under nitrogen. The mechanical properties of the cured polymer are measured with a Rheometrics Mechanical Spectrometer Model 605 and show a rubbery plateau above a glass transition temperature at 15° C. to 300° C. in the storage modulus, which indicates crosslinking. The cured polymer is transparent and possesses a rubbery resilience.

It is within the skill in the art to practice this invention in numerous modifications and variations in light of the above teachings It is, therefore, to be understood that changes may be made in the various described embodiments of this invention without departing from the spirit and scope of this invention as defined by the appended claims. For example, the various phases of the above described reaction may be conducted in a tank reactor, where reactants are continually entering and product is continually leaving the reaction vessel, or where each batch of reaction product is withdrawn from the vessel before another reaction is started. The phases may also be conducted in a tubular reactor, wherein the reaction system contains multiple reaction zones. It may also be desirable to purify 3-chloropentafluoropropene oxide to reduce the content therein of 1-chloro and 2-chloro isomers. Gravimetric means, such as a separatory funnel, may be used to isolate the product instead of flashing and/or distillation.

What is claimed is:

1. A process for preparing an ether described by the formula

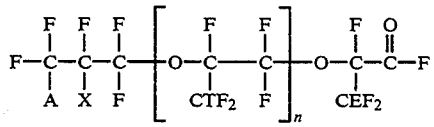

where A, T and E are each independently a fluorine, chlorine, bromine or iodine atom, X is a chlorine, bromine or iodine atom, and n is 0 to 6, comprising
   (a) preparing a 2,3-dihaloperfluoropropionyl fluoride by contacting an alkali metal chloride, bromide or iodide with a 3-haloperfluoropropene oxide in an inert liquid reaction medium,
   (b) coupling said 2,3-dihaloperfluoropropionyl fluoride to a 3-haloperfluoropropene oxide,
   (c) coupling the product of step (b) to n equivalents of a 3-haloperfluoropropene oxide, and
   (d) recovering the above described ether.

2. A process for preparing a vinyl ether described by the formula

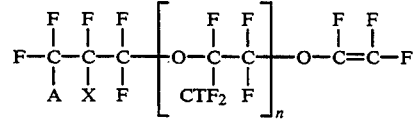

where A and T are each independently a fluorine, chlorine, bromine or iodine atom, X is a chlorine, bromine or iodine atom, and n is 0 to 6, comprising
   (a) preparing a 2,3-dihaloperfluoropropionyl fluoride by contacting an alkali metal chloride, bromide or iodide with a 3-haloperfluoropropene oxide in an inert liquid reaction medium,
   (b) coupling said 2,3-dihaloperfluoropropionyl fluoride to a 3-haloperfluoropropene oxide,
   (c) coupling the product of step (b) to n equivalents of a 3-haloperfluoropropene oxide,
   (d) decarboxylating the product of step (c), and
   (e) recovering said vinyl ether.

3. A process for preparing an allyl vinyl ether described by the formula

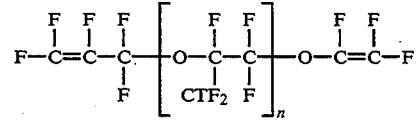

where T is a fluorine, chlorine, bromine or iodine atom, and n is 0 to 6, comprising
   (a) preparing a 2,3-dihaloperfluoropropionyl fluoride by contacting an alkali metal chloride, bromide or iodide with a 3-haloperfluoropropene oxide in an inert liquid reaction medium,
   (b) coupling said 2,3-dihaloperfluoropropionyl fluoride to a 3-haloperfluoropropene oxide, (c) coupling the product of step (b) to n equivalents of a 3-haloperfluoropropene oxide, (d) decarboxylating the product of step (c), (e) dehalogenating the product of step (d), and (f) recovering said allyl vinyl ether.

4. The process of claim 2 or 3 wherein the 3-haloperfluoropropene oxide is perfluoropropene oxide.

5. The process of claim 1, 2 or 3 wherein the 3-haloperfluoropropene oxide is 3-chloroperfluoropropene oxide.

6. The process of claim 2 or 3 wherein the 3-haloperfluoropropene oxide is 3-bromoperfluoropropene oxide.

7. The process of claim 1,2 or 3 wherein step (b) comprises contacting said 2,3-dihaloperfluoropropionyl fluoride with an alkali metal fluoride and a 3-haloperfluoropropene oxide in admixture in an inert liquid reaction medium.

8. The process of claim 1,2 or 3 wherein step (c) comprises contacting the product of step (b) with an alkali metal fluoride and n equivalents of a 3-haloperfluoropropene oxide in admixture in an inert liquid reaction medium.

9. The process of claim 1,2 or 3 wherein the alkali metal ion is lithium.

10. The process of claim 7 wherein the alkali metal ion is lithium.

11. The process of claim 8 wherein the alkali metal ion is lithium.

12. The process of claim 2 or 3 wherein the alkali metal ion is sodium.

13. The process of claim 7 wherein the alkali metal ion is sodium.

14. The process of claim 8 wherein the alkali metal ion is sodium.

15. The process of claim 1,2 or 3 wherein the alkali metal chloride, bromide or iodide is an alkali metal chloride.

16. The process of claim 2 or 3 wherein the alkali metal chloride, bromide or iodide is an alkali metal bromide.

17. The process of claim 3 wherein the inert liquid reaction medium is selected from the group consisting of a sulfone and a glycol diether.

18. The process of claim 7 wherein the inert liquid reaction medium is selected from the group consisting of a sulfone and a glycol diether.

19. The process of claim 8 wherein the inert liquid reaction medium is selected from the group consisting of a sulfone and a glycol diether.

20. The process of claim 2 or 3 wherein step (d) comprises contacting the product of step (c) with an oxygen-containing salt of an alkali or alkaline earth metal in admixture in an inert liquid reaction medium.

21. The process of claim 20 wherein the oxygen-containing salt is selected from the group consisting of an alkali metal carbonate, sulfate, sulfite, phosphate, phosphite, nitrate, nitrite and silicate.

22. The process of claim 20 wherein the oxygen-containing salt is selected from the group consisting of an alkaline earth metal carbonate, sulfate, sulfite, phosphate, phosphite, nitrate, nitrite and silicate.

23. The process of claim 20 wherein the oxygen-containing salt is sodium carbonate.

24. The process of claim 20 wherein the inert liquid reaction medium is selected from the group consisting of a sulfone and a glycol diether.

25. The process of claim 3 wherein step (e) comprises contacting said the product of step (d) with a metal dehalogenating agent in admixture in an inert liquid reaction medium.

26. The process of claim 25 wherein said metal dehalogenating agent is selected from the group consisting of zinc and magnesium.

27. The process of claim 25 further comprising agitating the reaction mixture with ultrasonic radiation.

28. The process of claim 25 wherein said inert liquid reaction medium is selected from the group consisting of 1-methyl-2-pyrolidone, dimethylsulfoxide, N,N-dimethylacetamide and N,N-dimethylformamide.

29. The process of claim 2 or 3 wherein n is 1.

30. The process of claim 2 or 3 wherein n is 2 to 6.

31. A process for preparing a 3,6-dioxa-5-halodifluoromethyl-8,9-dihaloperfluoro-1-nonene, comprising (a) adding a distilled 2-[2'-(2'',3''-dichloropentafluoropropoxy)hexafluoropropoxy]-3-chlorotrifluoropropionyl fluoride dropwise to sodium carbonate slurried in sulfolane at 45°–52° C. to form a mixture, (b) heating the mixture with vigorous stirring to 80°–81° C. until the evolution of carbon dioxide has ceased, (c) cooling the mixture, and (d) distilling said mixture under vacuum to collect a 3,6-dioxa-5-halodifluoromethyl-8,9-dihaloperfluoro-1-nonene in a receiver cooled with a dry ice-acetone mixture.

32. A process for preparing a 3,6-dioxa-5-halodifluoromethylperfluoronona-1,8-diene, comprising (a) covering zinc dust with a dry, inert liquid reaction medium to form a reaction mixture, (b) irradiating the reaction mixture with an ultrasonic wave, (c) adding distilled 3,6-dioxa-5-trifluoromethyl-8,9-dichloroperfluoro-1-nonene to the reaction mixture dropwise over 1 hour at 32°–48° C., and (d) distilling the reaction mixture under vacuum at ambient temperature to collect a 3,6-dioxa-5-halodifluoromethylperfluoronona-1,8-diene in a receiver cooled with a dry ice-acetone mixture.

* * * * *